United States Patent
Bujard et al.

(10) Patent No.: US 9,963,593 B2
(45) Date of Patent: *May 8, 2018

(54) INTERFERENCE PIGMENTS ON THE BASIS OF PERLITE FLAKES

(71) Applicant: BASF Corporation, Florham Park, NJ (US)

(72) Inventors: Patrice Bujard, Courtepin (CH); Philippe Bugnon, Le Mouret (CH); Marc Baysang, Busserach (CH)

(73) Assignee: BASF CORPORATION, Florham Park, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/173,640

(22) Filed: Jun. 4, 2016

(65) Prior Publication Data

US 2016/0280926 A1    Sep. 29, 2016

Related U.S. Application Data

(63) Continuation of application No. 12/668,028, filed as application No. PCT/EP2008/058160 on Jun. 26, 2008, now abandoned.

(30) Foreign Application Priority Data

Jul. 12, 2007 (EP) .................................... 07112337

(51) Int. Cl.
| | | |
|---|---|---|
| *C09C 1/00* | (2006.01) | |
| *A61K 8/02* | (2006.01) | |
| *A61K 8/26* | (2006.01) | |
| *A61Q 1/02* | (2006.01) | |
| *C08K 9/02* | (2006.01) | |
| *C09D 5/36* | (2006.01) | |
| *C09D 11/037* | (2014.01) | |
| *C09D 17/00* | (2006.01) | |

(52) U.S. Cl.
CPC .......... *C09C 1/0024* (2013.01); *A61K 8/0254* (2013.01); *A61K 8/0266* (2013.01); *A61K 8/26* (2013.01); *A61Q 1/02* (2013.01); *C08K 9/02* (2013.01); *C09C 1/0015* (2013.01); *C09C 1/0021* (2013.01); *C09C 1/0078* (2013.01); *C09D 5/36* (2013.01); *C09D 11/037* (2013.01); *C09D 17/008* (2013.01); *A61K 2800/10* (2013.01); *A61K 2800/63* (2013.01); *A61K 2800/651* (2013.01); *C01P 2004/54* (2013.01); *C01P 2004/61* (2013.01); *C01P 2006/80* (2013.01); *C08K 2201/014* (2013.01); *C09C 2200/102* (2013.01); *C09C 2200/301* (2013.01); *C09C 2200/302* (2013.01); *C09C 2200/303* (2013.01); *C09C 2200/306* (2013.01); *C09C 2220/10* (2013.01); *C09C 2220/106* (2013.01)

(58) Field of Classification Search
None
See application file for complete search history.

(56) References Cited

U.S. PATENT DOCUMENTS

| | | | |
|---|---|---|---|
| 3,536,520 | A | 10/1970 | Hanke et al. |
| 3,553,001 | A | 1/1971 | Kohlschutter et al. |
| 4,948,631 | A | 8/1990 | Ostertag et al. |
| 5,759,255 | A | 6/1998 | Venturini et al. |
| 5,877,895 | A | 3/1999 | Shaw et al. |
| 7,566,499 | B2 | 7/2009 | Kishimoto et al. |
| 8,034,404 | B2 | 10/2011 | Kishimoto et al. |
| 2010/0154680 | A1 | 6/2010 | Friedrich et al. |

FOREIGN PATENT DOCUMENTS

| | | |
|---|---|---|
| DE | 20 09 566 | 11/1971 |
| DE | 22 14 545 | 3/1972 |
| DE | 22 15 191 | 10/1972 |
| DE | 22 44 298 | 3/1974 |
| DE | 23 13 331 | 9/1974 |
| DE | 23 13 332 | 9/1974 |
| DE | 24 29 762 | 1/1976 |
| DE | 25 22 572 | 12/1976 |
| DE | 29 28 287 | 1/1981 |
| DE | 31 37 808 | 3/1983 |
| DE | 31 37 809 | 3/1983 |
| DE | 31 51 343 | 7/1983 |
| DE | 31 51 354 | 7/1983 |
| DE | 31 51 355 | 7/1983 |
| DE | 32 11 602 | 10/1983 |
| DE | 32 35 017 | 3/1984 |
| DE | 34 33 657 | 3/1985 |
| DE | 33 34 598 | 4/1985 |
| DE | 40 30 727 | 4/1992 |
| DE | 41 40 900 | 6/1993 |
| DE | 42 36 332 | 5/1994 |

(Continued)

OTHER PUBLICATIONS

Notification of Reasons for Refusal in JP Pat. Appl. No. 2014-204330, dated Oct. 3, 2016 (English translation—6 pages).

(Continued)

*Primary Examiner* — Nissa Westerberg

(74) *Attorney, Agent, or Firm* — Foley & Lardner LLP

(57) ABSTRACT

The present invention relates to pigments, comprising a plate-like substrate of perlite, and (a) a dielectric material, especially a metal oxide, having a high index of refraction; and/or (a) a metal layer, especially a thin semi-transparent metal layer; a process for their production and their use in paints, ink jet printing, for dyeing textiles, for pigmenting coatings (paints), printing inks, plastics, cosmetics, glazes for ceramics and glass.

16 Claims, No Drawings

(56) References Cited

FOREIGN PATENT DOCUMENTS

| | | |
|---|---|---|
| DE | 44 03 678 | 8/1995 |
| DE | 19501307 | 7/1996 |
| DE | 19516181 | 7/1996 |
| DE | 19843014 | 3/2000 |
| EP | 0 458 51 | 2/1982 |
| EP | 0 106 235 | 4/1984 |
| EP | 0 141 173 | 5/1985 |
| EP | 0 268 918 | 6/1988 |
| EP | 0 332 071 | 9/1989 |
| EP | 0 338 428 | 10/1989 |
| EP | 0 388 932 | 9/1990 |
| EP | 0 402 943 | 12/1990 |
| EP | 0 632 109 | 1/1995 |
| EP | 0 649 886 | 4/1995 |
| EP | 0 678 561 | 10/1995 |
| EP | 0 707 050 | 4/1996 |
| EP | 0 735 114 | 10/1996 |
| EP | 0 741 170 | 11/1996 |
| EP | 0 753 545 | 1/1997 |
| EP | 0 892 832 | 1/1999 |
| EP | 1 213 330 | 6/2002 |
| EP | 1 467 468 | 10/2004 |
| EP | 1 548 071 | 6/2005 |
| EP | 1 959 988 | 8/2008 |
| JP | 02-123165 A | 5/1990 |
| JP | 11-012488 | 1/1999 |
| JP | 2004-346272 | 12/2004 |
| JP | 2010-059422 | 3/2010 |
| WO | WO-93/08237 | 4/1993 |
| WO | WO-93/12182 | 6/1993 |
| WO | WO-93/19131 | 9/1993 |
| WO | WO-97/29059 | 8/1997 |
| WO | WO-98/12266 | 3/1998 |
| WO | WO-98/38254 | 9/1998 |
| WO | WO-98/53011 | 11/1998 |
| WO | WO-99/20695 | 4/1999 |
| WO | WO-99/57204 | 11/1999 |
| WO | WO-00/12634 | 3/2000 |
| WO | WO-00/42111 | 7/2000 |
| WO | WO-02/11882 | 2/2002 |
| WO | WO-03/006558 | 1/2003 |
| WO | WO-03/037993 | 5/2003 |
| WO | WO-2004/031305 | 4/2004 |
| WO | WO-2006/131472 | 12/2006 |
| WO | WO-2007/054379 | 5/2007 |

OTHER PUBLICATIONS

Cherepanina, Glass and Ceramics, (1965), 22(6), pp. 371-372.
Final Office Action received for U.S. Appl. No. 12/668,028 dated Dec. 28, 2012, 10 pages.
Liu, Hetian, "The Application of Perlite in Ceramic Pigments," Ceramics, (1974), vol. 1, pp. 50-51 (English translation 2 pages).
Machine English Language Translation of JP 11-012488 (1999), 12 pages.
Non-Final Office Action received for U.S. Appl. No. 12/668,028 dated May 31, 2012, 16 pages.
Pfaff, Gerhard et al., "Angle-Dependent Optical Effects Deriving from Submicron Structures of Films and Pigments," Chem. Rev., (1999), vol. 99, No. 7, pp. 1963-1982.

INTERFERENCE PIGMENTS ON THE BASIS OF PERLITE FLAKES

CROSS-REFERENCE TO RELATED PATENT APPLICATIONS

This application is a U.S. continuation patent application claiming the benefit of U.S. patent application Ser. No. 12/668,028, filed on Apr. 21, 2010, which in turn is a U.S. 3.71 National Stage Application of International Application PCT/EP2008/058160, filed on Jun. 26, 2008, which in turn claims the benefit of EP 07112337.6 filed Jul. 12, 2007, the entire contents of all of which are incorporated by reference in their entireties.

The present invention relates to (interference) pigments having a core of perlite, comprising a metal oxide having a high index of refraction or a (thin semi-transparent) metal layer, a method of producing the (interference) pigments and their use in paints, ink-jet printing, for dyeing textiles, for pigmenting coatings, printing inks, plastics, cosmetics, glazes for ceramics and glass.

Interference pigments having a core consisting of a transparent carrier material, such as, for example, natural, or synthetic mica, $SiO_2$, or glass, are known. Reference is made, for example, to Gerhard Pfaff and Peter Reynders, Chem. Rev. 99 (1999) 1963-1981.

Naturally transparent mica is used in most cases as substrate. Natural mica is biological inert and consequently it is acceptable for a wide range of applications. The substrate mica consists of thin platelets having a thickness of about 300 to 600 nm and a defined particle size distribution.

Pearlescent pigments on basis of natural mica coated with a metal oxide such as iron oxide, titanium oxide, etc. are disadvantageous in that they develop yellow color specific to mica at mass tone angle or shade side due to iron oxide impurities, and that interference effect is weak due to the large thickness distribution of the mica substrate and the unevenness of the surface of the mica substrate.

The object of the present invention was to develop additional pearlescent pigments on basis of a natural substrate that would exhibit the well-known advantages of mica pigments (e.g. good application properties in a variety of binder systems, environmental compatibility and simple handling) with the possibility of realizing superior optical effects, i.e. to provide interference pigments, having high color strength and/or color purity based on a natural substrate.

Said object has been solved by pigments, comprising a plate-like substrate of perlite, and (a) a dielectric material, especially a metal oxide, having a high index of refraction; and/or (a) a metal layer, especially a thin semi-transparent metal layer.

The pigment particles generally have a length of from 2 μm to 5 mm, a width of from 2 μm to 2 mm, and an average thickness of <4 μm, and a ratio of length to thickness of at least 5:1, and contain a core of perlite, having two substantially parallel faces, the distance between which is the shortest axis of the core. The perlite core is either coated with a dielectric material, especially a metal oxide, having a high index of refraction, or a metal layer, especially a thin semi-transparent metal layer. Said layers can be coated with additional layers.

Suitable metals for the (semi-transparent) metal layer are, for example, Cr, Ti, Mo, W, Al, Cu, Ag, Au, or Ni. The semi-transparent metal layer has typically a thickness of between 5 and 25 nm, especially between 5 and 15 nm.

According to the present invention the term "aluminum" comprises aluminum and alloys of aluminum. Alloys of aluminum are, for example described in G. Wassermann in Ullmanns Enzyklopädie der Industriellen Chemie, 4. Auflage, Verlag Chemie, Weinheim, Band 7, S. 281 to 292. Especially suitable are the corrosion stable aluminum alloys described on page 10 to 12 of WO00/12634, which comprise besides of aluminum silicon, magnesium, manganese, copper, zinc, nickel, vanadium, lead, antimony, tin, cadmium, bismuth, titanium, chromium and/or iron in amounts of less than 20% by weight, preferably less than 10% by weight.

The metal layer can be obtained by wet chemical coating or by chemical vapor deposition, for example, gas phase deposition of metal carbonyls. The substrate is suspended in an aqueous and/or organic solvent containing medium in the presence of a metal compound and is deposited onto the substrate by addition of a reducing agent. The metal compound is, for example, silver nitrate or nickel acetyl acetonate (WO03/37993).

According to U.S. Pat. No. 3,536,520 nickel chloride can be used as metal compound and hypophosphite can be used as reducing agent. According to EP-A-353544 the following compounds can be used as reducing agents for the wet chemical coating: aldehydes (formaldehyde, acetaldehyde, benzalaldehyde), ketones (acetone), carbonic acids and salts thereof (tartaric acid, ascorbinic acid), reductones (isoascorbinic acid, triosereductone, reductine acid), and reducing sugars (glucose). However, it is also possible to use reducing alcohols (allyl alcohol), polyols and polyphenols, sulfites, hydrogensulfites, dithionites, hypophosphites, hydrazine, boron nitrogen compounds, metal hydrides and complex hydrides of aluminium and boron. The deposition of the metal layer can furthermore be carried out with the aid of a CVD method. Methods of this type are known. Fluidised-bed reactors are preferably employed for this purpose. EP-A-0741170 describes the deposition of aluminium layers by reduction of alkylaluminium compounds using hydrocarbons in a stream of inert gas. The metal layers can furthermore be deposited by gas-phase decomposition of the corresponding metal carbonyls in a heatable fluidised-bed reactor, as described in EP-A-045851. Further details on this method are given in WO93/12182. A further process for the deposition of thin metal layers, which can be used in the present case for the application of the metal layer to the substrate, is the known method for vapour deposition of metals in a high vacuum. It is described in detail in Vakuum-Beschichtung [Vacuum Coating], Volumes 1-5; Editors Frey, Kienel and Löbl, VDI-Verlag, 1995. In the sputtering process, a gas discharge (plasma) is ignited between the support and the coating material, which is in the form of plates (target). The coating material is bombarded with high-energy ions from the plasma, for example argon ions, and thus removed or atomised. The atoms or molecules of the atomised coating material are precipitated on the support and form the desired thin layer. The sputtering process is described in Vakuum-Beschichtung [Vacuum Coating], Volumes 1-5; Editors Frey, Kienel and Löbl, VDI-Verlag, 1995. For use in outdoor applications, in particular in the application in vehicle paints, the pigments can be provided with an additional weather-stabilising protective layer, the so-called post-coating, which simultaneously effects optimum adaptation to the binder system. Post-coatings of this type have been described, for example, in EP-A-0268918 and EP-A-0632109.

If pigments with metallic appearance are desired, the thickness of the metal layer is >25 nm to 100 nm, preferably 30 to 50 nm. If pigments with colored metal effects are desired, additional layers of colored or colorless metal oxides, metal nitrides, metal sulfides and/or metals can be deposited. These layers are transparent or semi-transparent. It is preferred that layers of high index of refraction and layers of low index of refraction alternate or that one layer is present, wherein within the layer the index of refraction is gradually changing. It is possible for the weathering resistance to be increased by means of an additional coating, which at the same time causes an optimal adaption to the binder system (EP-A-268918 and EP-A-632109).

The metal and/or metal oxide coated perlite flakes can be, as described in WO06/131472, treated with a plasma torch. The treatment promotes, for example, uniform crystallinity and/or coating densification. The rapid melting and solidification for certain particles can provide enhanced properties associated with the metal and/or metal oxide coating such as barrier properties, binding properties and crystalline surface formation. The short residence times in the reaction zones allow for rapid treatments. Further the processing conditions can be adjusted to selective melt and resolidificate and crystallize the surface and near surface of the particles. Moreover, surface leveling can be achieved which results in a uniform surface with minimal defects. Among other things, this may help to avoid agglomeration of particles.

The process comprises
(A) providing coated perlite flakes,
(B) entraining said coated perlite flakes in a stream of gas for transport to a plasma torch;
(C) creating a plasma in said stream of gas to heat the outer surface of the coated perlite flakes;
(D) permitting said coated perlite flakes to cool; and
(E) collecting said coated perlite flakes.

The plasma torch is preferably an induction plasma torch. The preferred induction plasma torches for use in the process of the present invention are available from Tekna Plasma Systems, Inc. of Sherbrooke, Quebec, Canada. Boulos et al., U.S. Pat. No. 5,200,595, is hereby incorporated by reference for its teachings relative to the construction and operation of plasma induction torches.

In one preferred embodiment of the present invention, the pigments comprise on the perlite substrate
(a) a dielectric layer,
(b) a metal layer, and
(c) a dielectric layer. Such pigments have high infrared reflectivity and high visible transmission.

Preferably, metallic silver is used as the metal layer because it offers high reflectivity to infrared radiation together with high transmission to solar radiation providing its reflection losses are minimized. Although high purity metallic silver films are preferred, certain impurities and/or alloying metals can be tolerated as long as they do not significantly reduce the infrared reflectivity or significantly increase the visible absorptivity. The thickness of the metallic silver layer is within a range of from 3 to 20 nm.

Suitable materials for layer (c) are materials which are transparent to solar and infrared radiation in the thicknesses used. Additionally, these materials serve as anti-reflection coatings to minimize the reflection of visible light by the silver layer, and these materials preferably have high indices of refraction. Some suitable materials for layer (c) include, but are not limited to, titanium dioxide, silicon dioxide, silicon monoxide, bismuth oxide, tin oxide, indium oxide, chromium oxide, zinc sulfide and magnesium fluoride. Titanium dioxide is a preferred material because of its high refractive index and because it has been found to have minimum interdiffusion with silver.

Suitable materials for layer (a) are transparent materials which cooperate with layer (b) to minimize visible light reflection losses by the silver layer. The transparent materials suitable for layer (c) are also suitable for layer (a), and titanium dioxide is also a preferred material for this layer. Layer (a) can be formed from the same material as layer (c), or from a different material in which case it would probably have a different thickness.

The thicknesses for layer (c) and layer (a) are chosen to maximize solar transmission and infrared reflectivity. It has been found that a thickness of from about 15 to about 50 nm is suitable for layer (c). The thickness of layer (a) is then chosen based upon a number of considerations such as whether it is desired to achieve the optimum solar transmission, the optimum ratio of transmission to thermal reflectivity or some combination between these optimized values.

In most cases, the optical properties desired can be achieved by choosing a thickness of layer of between about 15 nm and about 50 nm.

In one preferred embodiment of the present invention, the interference pigments comprise materials having a "high" index of refraction, which is defined herein as an index of refraction of greater than about 1.65, and optionally materials having a "low" index of refraction, which is defined herein as an index of refraction of about 1.65 or less. Various (dielectric) materials that can be utilized including inorganic materials such as metal oxides, metal suboxides, metal fluorides, metal oxyhalides, metal sulfides, metal chalcogenides, metal nitrides, metal oxynitrides, metal carbides, combinations thereof, and the like, as well as organic dielectric materials. These materials are readily available and easily applied by physical, or chemical vapor deposition processes, or by wet chemical coating processes.

Optionally a $SiO_2$ layer can be arranged between the perlite substrate and the materials having a "high" index of refraction. By applying a $SiO_2$ layer on the perlite substrate the perlite surface is protected against chemical alteration, such as, for example, swelling and leaching of perlite components. The thickness of the $SiO_2$ layer is in the range of 5 to 200 nm, especially 20 to 150 nm. The $SiO_2$ layer is preferably prepared by using an organic silane compound, such as tetraethoxy silane (TEOS). The $SiO_2$ layer can be replaced by thin layers (thickness 1 to 20 nm) of $Al_2O_3$, $Fe_2O_3$ or $ZrO_2$.

Furthermore, the $SiO_2$-coated, or $TiO_2$-coated perlite flakes may, as described in EP-A-0 982 376, be coated with a nitrogen-doped carbon layer. The process described in EP-A-0 982 376 comprises the following steps:
(a) suspending the $SiO_2$, or $TiO_2$ coated perlite flakes in a liquid,
(b) where appropriate adding a surface-modifier and/or a polymerization catalyst,
(c), before or after step (b), adding one or more polymers comprising nitrogen and carbon atoms, or one or more monomers capable of forming such polymers,
(d) forming a polymeric coating on the surface of the flakes,
(e) isolating the coated flakes and
(f) heating the coated flakes to a temperature of from 100 to 600° C. in a gaseous atmosphere.

The polymer may be a polypyrrole, a polyamide, a polyaniline, a polyurethane, a nitrile rubber or a melamine-formaldehyde resin, preferably a polyacrylonitrile, or the monomer is a pyrrole derivative, an acrylonitrile, a methacrylonitrile, a crotonitrile, an acrylamide, a methacrylamide or a crotonamide, preferably an acrylonitrile, methacrylonitrile or crotonitrile, most preferably an acrylonitrile.

Preferably, the flakes are heated in step (f) initially to from 100° C. to 300° C. in an oxygen-containing atmosphere and then to from 200 to 600° C. in an inert gas atmosphere.

The present invention therefore relates also to pigments based on the perlite flakes according to the invention comprising over the entire surface of the silicon oxide, or titanium oxide coated perlite flakes a layer consisting of from 50 to 95% by weight carbon, from 5 to 25% by weight nitrogen and from 0 to 25% by weight of the elements hydrogen, oxygen and/or sulfur, the percentage by weight data relating to the total weight of the layer (PAN).

The thickness of the nitrogen-doped carbon layer is generally from 10 to 150 nm, preferably from 30 to 70 nm. In said embodiment preferred pigments have the following layer structure: perlite substrate/$TiO_2$/PAN, perlite substrate/$TiO_2$/PAN/$TiO_2$, perlite substrate/$TiO_2$/PAN/$SiO_2$/PAN.

In an especially preferred embodiment, the interference pigments on the basis of the perlite substrate comprise a layer of a dielectric material having a "high" refractive index, that is to say a refractive index greater than about 1.65, preferably greater than about 2.0, most preferred greater than about 2.2, which is applied to the entire surface of the perlite substrate. Examples of such a dielectric material are zinc sulfide (ZnS), zinc oxide (ZnO), zirconium oxide ($ZrO_2$), titanium dioxide ($TiO_2$), carbon, indium oxide ($In_2O_3$), indium tin oxide (ITO), tantalum pentoxide ($Ta_2O_5$), chromium oxide ($Cr_2O_3$), cerium oxide ($CeO_2$), yttrium oxide ($Y_2O_3$), europium oxide ($Eu_2O_3$), iron oxides such as iron(II)/iron(III) oxide ($Fe_3O_4$) and iron(II) oxide ($Fe_2O_3$), hafnium nitride (HfN), hafnium carbide (HfC), hafnium oxide ($HfO_2$), lanthanum oxide ($La_2O_3$), magnesium oxide (MgO), neodymium oxide ($Nd_2O_3$), praseodymium oxide ($Pr_6O_{11}$), samarium oxide ($Sm_2O_3$), antimony trioxide ($Sb_2O_3$), silicon monoxides (SiO), selenium trioxide ($Se_2O_3$), tin oxide ($SnO_2$), tungsten trioxide ($WO_3$), or combinations thereof. The dielectric material is preferably a metal oxide. It being possible for the metal oxide to be a single oxide or a mixture of oxides, with or without absorbing properties, for example, $TiO_2$, $ZrO_2$, $Fe_2O_3$, $Fe_3O_4$, $Cr_2O_3$ or ZnO, with $TiO_2$ being especially preferred.

It is possible to obtain pigments that are more intense in colour and more transparent by applying, on top of the $TiO_2$ layer, a metal oxide of low refractive index, such as $SiO_2$, $Al_2O_3$, AlOOH, $B_2O_3$ or a mixture thereof, preferably $SiO_2$, and optionally applying a further $TiO_2$ layer on top of the latter layer (EP-A-892832, EP-A-753545, WO93/08237, WO98/53011, WO9812266, WO9838254, WO99/20695, WO00/42111, and EP-A-1213330). Nonlimiting examples of suitable low index dielectric materials that can be used include silicon dioxide ($SiO_2$), aluminum oxide ($Al_2O_3$), and metal fluorides such as magnesium fluoride ($MgF_2$), aluminum fluoride ($AlF_3$), cerium fluoride ($CeF_3$), lanthanum fluoride ($LaF_3$), sodium aluminum fluorides (e.g., $Na_3AlF_6$ or $Na_5Al_3F_{14}$), neodymium fluoride ($NdF_3$), samarium fluoride ($SmF_3$), barium fluoride ($BaF_2$), calcium fluoride ($CaF_2$), lithium fluoride (LiF), combinations thereof, or any other low index material having an index of refraction of about 1.65 or less. For example, organic monomers and polymers can be utilized as low index materials, including dienes or alkenes such as acrylates (e.g., methacrylate), polymers of perfluoroalkenes, polytetrafluoroethylene (TEFLON), polymers of fluorinated ethylene propylene (FEP), parylene, p-xylene, combinations thereof, and the like. Additionally, the foregoing materials include evaporated, condensed and cross-linked transparent acrylate layers, which may be deposited by methods described in U.S. Pat. No. 5,877,895, the disclosure of which is incorporated herein by reference.

Accordingly, preferred interference pigments comprise besides (a) a metal oxide of high refractive index in addition (b) a metal oxide of low refractive index, wherein the difference of the refractive indices is at least 0.1.

Pigments on the basis of perlite substrates, which have been coated by a wet chemical method, in the indicated order are particularly preferred:
$TiO_2$, $(SnO_2)TiO_2$ (substrate: perlite; layer: $(SnO_2)TiO_2$, preferably in the rutile modification), titanium suboxide, $TiO_2$/titanium suboxide, $Fe_2O_3$, $Fe_3O_4$, $TiFe_2O_5$, $Cr_2O_3$, $ZrO_2$, $Sn(Sb)O_2$, BiOCl, $Al_2O_3$, $Ce_2S_3$, $MoS_2$, $Fe_2O_3 \cdot TiO_2$ (substrate: perlite; mixed layer of $Fe_2O_3$ and $TiO_2$), $TiO_2$/$Fe_2O_3$ (substrate: perlite; first layer: $TiO_2$; second layer: $Fe_2O_3$), $TiO_2$/Berlin blau, $TiO_2$/$Cr_2O_3$, or $TiO_2$/$FeTiO_3$. In general the layer thickness ranges from 1 to 1000 nm, preferably from 1 to 300 nm.

In another particularly preferred embodiment the present invention relates to interference pigments containing at least three alternating layers of high and low refractive index, such as, for example, $TiO_2$/$SiO_2$/$TiO_2$, $(SnO_2)TiO_2$/$SiO_2$/$TiO_2$, $TiO_2$/$SiO_2$/$TiO_2$/$SiO_2$/$TiO_2$, $Fe_2O_3$/$SiO_2$/$TiO_2$, or $TiO_2$/$SiO_2$/$Fe_2O_3$.

Preferably the layer structure is as follows:
(a) a coating having a refractive index >1.65,
(b) a coating having a refractive index ≤1.65,
(c) a coating having a refractive index >1.65, and
(d) optionally an outer protective layer.

The thickness of the individual layers of high and low refractive index on the base substrate is essential for the optical properties of the pigment. The thickness of the individual layers, especially metal oxide layers, depends on the field of use and is generally 10 to 1000 nm, preferably 15 to 800 nm, in particular 20 to 600 nm.

The thickness of layer (A) is 10 to 550 nm, preferably 15 to 400 nm and, in particular, 20 to 350 nm. The thickness of layer (B) is 10 to 1000 nm, preferably 20 to 800 nm and, in particular, 30 to 600 nm. The thickness of layer (C) is 10 to 550 nm, preferably 15 to 400 nm and, in particular, 20 to 350 nm.

Particularly suitable materials for layer (A) are metal oxides, metal sulfides, or metal oxide mixtures, such as $TiO_2$, $Fe_2O_3$, $TiFe_2O_5$, $Fe_3O_4$, BiOCl, CoO, $Co_3O_4$, $Cr_2O_3$, $VO_2$, $V_2O_3$, $Sn(Sb)O_2$, $SnO_2$, $ZrO_2$, iron titanates, iron oxide hydrates, titanium suboxides (reduced titanium species having oxidation states from 2 to <4), bismuth vanadate, cobalt aluminate, and also mixtures or mixed phases of these compounds with one another or with other metal oxides. Metal sulfide coatings are preferably selected from sulfides of tin, silver, lanthanum, rare earth metals, preferably cerium, chromium, molybdenum, tungsten, iron, cobalt and/or nickel.

Particularly suitable materials for layer (B) are metal oxides or the corresponding oxide hydrates, such as $SiO_2$, $MgF_2$, $Al_2O_3$, AlOOH, $B_2O_3$ or a mixture thereof, preferably $SiO_2$.

Particularly suitable materials for layer (C) are colorless or colored metal oxides, such as $TiO_2$, $Fe_2O_3$, $TiFe_2O_5$, $Fe_3O_4$, BiOCl, CoO, $Co_3O_4$, $Cr_2O_3$, $VO_2$, $V_2O_3$, $Sn(Sb)O_2$, $SnO_2$, $ZrO_2$, iron titanates, iron oxide hydrates, titanium suboxides (reduced titanium species having oxidation states from 2 to <4), bismuth vanadate, cobalt aluminate, and also mixtures or mixed phases of these compounds with one another or with other metal oxides. The $TiO_2$ layers can additionally contain an absorbing material, such as carbon, selectively absorbing colorants, selectively absorbing metal cations, can be coated with absorbing material, or can be partially reduced.

Interlayers of absorbing or nonabsorbing materials can be present between layers (A), (B), (C) and (D). The thickness of the interlayers is 1 to 50 nm, preferably 1 to 40 nm and, in particular, 1 to 30 nm. Such an interlayer can, for example, consist of $SnO_2$. It is possible to force the rutile structure to be formed by adding small amounts of $SnO_2$ (see, for example, WO93/08237).

In this embodiment preferred interference pigments have the following layer structure:

| | | | |
|---|---|---|---|
| perlite | $TiO_2$ | $SiO_2$ | $TiO_2$ |
| perlite | $TiO_2$ | $SiO_2$ | $Fe_2O_3$ |
| perlite | $TiO_2$ | $SiO_2$ | $TiO_2 \cdot Fe_2O_3$ |
| perlite | $TiO_2$ | $SiO_2$ | $(Sn,Sb)O_2$ |
| perlite | $(Sn,Sb)O_2$ | $SiO_2$ | $TiO_2$ |
| perlite | $Fe_2O_3$ | $SiO_2$ | $(Sn,Sb)O_2$ |
| perlite | $TiO_2 \cdot Fe_2O_3$ | $SiO_2$ | $TiO_2 \cdot Fe_2O_3$ |
| perlite | $TiO_2$ | $SiO_2$ | $MoS_2$ |
| perlite | $TiO_2$ | $SiO_2$ | $Cr_2O_3$ |
| perlite | $Cr_2O_3$ | $SiO_2$ | $TiO_2$ |
| perlite | $Fe_2O_3$ | $SiO_2$ | $TiO_2$ |
| perlite | $TiO_2$ | $Al_2O_3$ | $TiO_2$ |
| perlite | $Fe_2TiO_5$ | $SiO_2$ | $TiO_2$ |
| perlite | $TiO_2$ | $SiO_2$ | $Fe_2TiO_5/TiO_2$ |
| perlite | TiO suboxides | $SiO_2$ | TiO suboxides |
| perlite | $TiO_2$ | $SiO_2$ | $TiO_2/SiO_2/TiO_2$ + Prussian Blue |
| perlite | $TiO_2$ | $SiO_2$ | $TiO_2/SiO_2/TiO_2$ |
| perlite | $TiO_2/SiO_2/TiO_2$ | $SiO_2$ | $TiO_2/SiO_2/TiO_2$ |

The metal oxide layers can be applied by CVD (chemical vapour deposition) or by wet chemical coating. The metal oxide layers can be obtained by decomposition of metal carbonyls in the presence of water vapour (relatively low molecular weight metal oxides such as magnetite) or in the presence of oxygen and, where appropriate, water vapour (e.g. nickel oxide and cobalt oxide). The metal oxide layers are especially applied by means of oxidative gaseous phase decomposition of metal carbonyls (e.g. iron pentacarbonyl, chromium hexacarbonyl; EP-A-45 851), by means of hydrolytic gaseous phase decomposition of metal alcoholates (e.g. titanium and zirconium tetra-n- and -iso-propanolate; DE-A-41 40 900) or of metal halides (e.g. titanium tetrachloride; EP-A-338 428), by means of oxidative decomposition of organyl tin compounds (especially alkyl tin compounds such as tetrabutyltin and tetramethyltin; DE-A-44 03 678) or by means of the gaseous phase hydrolysis of organyl silicon compounds (especially di-tert-butoxyacetoxysilane) described in EP-A-668 329, it being possible for the coating operation to be carried out in a fluidised-bed reactor (EP-A-045 851 and EP-A-106 235). $Al_2O_3$ layers (B) can advantageously be obtained by controlled oxidation during the cooling of aluminium-coated pigments, which is otherwise carried out under inert gas (DE-A-195 16 181).

Phosphate-, chromate- and/or vanadate-containing and also phosphate- and $SiO_2$-containing metal oxide layers can be applied in accordance with the passivation methods described in DE-A-42 36 332 and in EP-A-678 561 by means of hydrolytic or oxidative gaseous phase decomposition of oxide-halides of the metals (e.g. $CrO_2Cl_2$, $VOCl_3$), especially of phosphorus oxyhalides (e.g. $POCl_3$), phosphoric and phosphorous acid esters (e.g. di- and tri-methyl and di- and tri-ethyl phosphite) and of amino-group-containing organyl silicon compounds (e.g. 3-aminopropyl-triethoxy- and -trimethoxy-silane).

Layers of oxides of the metals zirconium, titanium, iron and zinc, oxide hydrates of those metals, iron titanates, titanium suboxides or mixtures thereof are preferably applied by precipitation by a wet chemical method, it being possible, where appropriate, for the metal oxides to be reduced. In the case of the wet chemical coating, the wet chemical coating methods developed for the production of pearlescent pigments may be used; these are described, for example, in DE-A-14 67 468, DE-A-19 59 988, DE-A-20 09 566, DE-A-22 14 545, DE-A-22 15 191, DE-A-22 44 298, DE-A-23 13 331, DE-A-25 22 572, DE-A-31 37 808, DE-A-31 37 809, DE-A-31 51 343, DE-A-31 51 354, DE-A-31 51 355, DE-A-32 11 602 and DE-A-32 35 017, DE 195 99 88, WO 93/08237, WO 98/53001 and WO03/6558.

The metal oxide of high refractive index is preferably $TiO_2$ and/or iron oxide, and the metal oxide of low refractive index is preferably $SiO_2$. Layers of $TiO_2$ can be in the rutile or anastase modification, wherein the rutile modification is preferred. $TiO_2$ layers can also be reduced by known means, for example ammonia, hydrogen, hydrocarbon vapor or mixtures thereof, or metal powders, as described in EP-A-735,114, DE-A-3433657, DE-A-4125134, EP-A-332071, EP-A-707,050, WO93/19131, or WO06/131472.

For the purpose of coating, the substrate particles are suspended in water and one or more hydrolysable metal salts are added at a pH suitable for the hydrolysis, which is so selected that the metal oxides or metal oxide hydrates are precipitated directly onto the particles without subsidiary precipitation occurring. The pH is usually kept constant by simultaneously metering in a base. The pigments are then separated off, washed, dried and, where appropriate, calcinated, it being possible to optimise the calcinating temperature with respect to the coating in question. If desired, after individual coatings have been applied, the pigments can be separated off, dried and, where appropriate, calcinated, and then again re-suspended for the purpose of precipitating further layers.

The metal oxide layers are also obtainable, for example, in analogy to a method described in DE-A-195 01 307, by producing the metal oxide layer by controlled hydrolysis of one or more metal acid esters, where appropriate in the presence of an organic solvent and a basic catalyst, by means of a sol-gel process. Suitable basic catalysts are, for example, amines, such as triethylamine, ethylenediamine, tributylamine, dimethylethanolamine and methoxy-propylamine. The organic solvent is a water-miscible organic solvent such as a $C_{1-4}$alcohol, especially isopropanol.

Suitable metal acid esters are selected from alkyl and aryl alcoholates, carboxylates, and carboxyl-radical- or alkyl-radical- or aryl-radical-substituted alkyl alcoholates or carboxylates of vanadium, titanium, zirconium, silicon, aluminium and boron. The use of triisopropyl aluminate, tetraisopropyl titanate, tetraisopropyl zirconate, tetraethyl orthosilicate and triethyl borate is preferred. In addition, acetylacetonates and acetoacetylacetonates of the aforementioned metals may be used. Preferred examples of that type of metal acid ester are zirconium acetylacetonate, aluminium acetylacetonate, titanium acetylacetonate and diisobutyloleyl acetoacetylaluminate or diisopropyloleyl acetoacetylacetonate and mixtures of metal acid esters, for example Dynasil® (Hüls), a mixed aluminium/silicon metal acid ester.

As a metal oxide having a high refractive index, titanium dioxide is preferably used, the method described in U.S. Pat. No. 3,553,001 being used, in accordance with an embodiment of the present invention, for application of the titanium dioxide layers.

An aqueous titanium salt solution is slowly added to a suspension of the material being coated, which suspension has been heated to about 50-100° C., especially 70-80° C., and a substantially constant pH value of about from 0.5 to 5, especially about from 1.2 to 2.5, is maintained by simultaneously metering in a base such as, for example, aqueous ammonia solution or aqueous alkali metal hydroxide solution. As soon as the desired layer thickness of precipitated $TiO_2$ has been achieved, the addition of titanium salt solution and base is stopped. Addition of a precursor for $Al_2O_3$ or MgO in the starting solutions is a way for improving the morphology of the $TiO_2$ layer.

This method, also referred to as the "titration method", is distinguished by the fact that an excess of titanium salt is avoided. That is achieved by feeding in for hydrolysis, per unit time, only that amount which is necessary for even coating with the hydrated $TiO_2$ and which can be taken up per unit time by the available surface of the particles being coated. In principle, the anatase form of $TiO_2$ forms on the surface of the starting pigment. By adding small amounts of $SnO_2$, however, it is possible to force the rutile structure to be formed. For example, as described in WO 93/08237, tin dioxide can be deposited before titanium dioxide precipitation and the product coated with titanium dioxide can be calcined at from 800 to 900° C.

In an especially preferred embodiment of the present invention the perlite flakes are mixed with distilled water in a closed reactor and heated at about 90° C. The pH is set to about 1.8 to 2.2 and a preparation comprising $TiOCl_2$, HCl, glycine and distilled water is added slowly while keeping the pH constant (1.8 to 2.2) by continuous addition of 1M NaOH solution. Reference is made to European patent application PCT/EP2008/051910. By adding an amino acid, such as glycine, during the deposition of the $TiO_2$ it is possible to improve the quality of the $TiO_2$ coating to be formed. Advantageously, a preparation comprising $TiOCl_2$, HCl, and glycine and distilled water is added to the substrate flakes in water.

The $TiO_2$ can optionally be reduced by usual procedures: U.S. Pat. No. 4,948,631 ($NH_3$, 750-850° C.), WO93/19131 ($H_2$, >900° C.) or DE-A-19843014 (solid reduction agent, such as, for example, silicon, >600° C.).

Where appropriate, an $SiO_2$ (protective) layer can be applied on top of the titanium dioxide layer, for which the following method may be used: A soda waterglass solution is metered into a suspension of the material being coated, which suspension has been heated to about 50-100° C., especially 70-80° C. The pH is maintained at from 4 to 10, preferably from 6.5 to 8.5, by simultaneously adding 10% hydrochloric acid. After addition of the waterglass solution, stirring is carried out for 30 minutes.

It is possible to obtain pigments that are more intense in colour and more transparent by applying, on top of the $TiO_2$ layer, a metal oxide of "low" refractive index, that is to say a refractive index smaller than about 1.65, such as $SiO_2$, $Al_2O_3$, AlOOH, $B_2O_3$ or a mixture thereof, preferably $SiO_2$, and applying a further $Fe_2O_3$ and/or $TiO_2$ layer on top of the latter layer. Such multi-coated interference pigments comprising a perlite substrate and alternating metal oxide layers of with high and low refractive index can be prepared in analogy to the processes described in WO98/53011 and WO99/20695.

It is, in addition, possible to modify the powder colour of the pigment by applying further layers such as, for example, coloured metal oxides or Berlin Blue, compounds of transition metals, e.g. Fe, Cu, Ni, Co, Cr, or organic compounds such as dyes or colour lakes.

In addition, the pigment according to the invention can also be coated with poorly soluble, firmly adhering, inorganic or organic colourants. Preference is given to the use of colour lakes and, especially, aluminium colour lakes. For that purpose an aluminium hydroxide layer is precipitated, which is, in a second step, laked by using a colour lake (DE-A-24 29 762 and DE-A-29 28 287).

Furthermore, the pigment according to the invention may also have an additional coating with complex salt pigments, especially cyanoferrate complexes (EP-A-141 173 and DE-A-23 13 332).

To enhance the weather and light stability the (multilayer) perlite flakes can be, depending on the field of application, subjected to a surface treatment. Useful surface treatments are, for example, described in DE-A-2215191, DE-A-3151354, DE-A-3235017, DE-A-3334598, DE-A-4030727, EP-A-649886, WO97/29059, WO99/57204, and U.S. Pat. No. 5,759,255. Said surface treatment might also facilitate the handling of the pigment, especially its incorporation into various application media.

In a preferred embodiment of the present invention is directed to pigments which contain a core of perlite and comprise a mixed layer of $Al_2O_3/TiO_2$. The mixed layer can contain up to 20 mol % $Al_2O_3$. The mixed layer of $Al_2O_3/TiO_2$ is obtained by slowly adding an aqueous aluminum and titanium salt solution to a suspension of the material being coated, which suspension has been heated to about 50-100° C., especially 70-80° C., and maintaining a substantially constant pH value of about from 0.5 to 5, especially about from 1.2 to 2.5, by simultaneously metering in a base such as, for example, aqueous ammonia solution or aqueous alkali metal hydroxide solution. As soon as the desired layer thickness of precipitated $Al_2O_3/TiO_2$ has been achieved, the addition of titanium and aluminum salt solution and base is stopped.

The thickness of the mixed layer of $Al_2O_3/TiO_2$ is in general in the range of 20 to 200 nm, especially 50 to 150 nm. Preferably the pigments comprise a $TiO_2$ layer on top of the mixed layer of $Al_2O_3/TiO_2$ having a thickness of 1 to 50 nm, especially 10 to 20 nm. By varying the thickness of the mixed layer of $Al_2O_3/TiO_2$ the flop of the pigments can be enhanced and controlled as desired.

In another preferred embodiment of the present invention is directed to pigments which contain a core of perlite and consist of subsequent layers of $TiO_2/SnO_2/TiO_2$, wherein the $TiO_2$ layer next to the perlite substrate has a thickness of 1 to 20 nm and is preferably prepared by using titanium alcoholates, especially tetraisopropyl titanate.

The platelet-like substrate (core) of the pigments of the present invention consists of perlite.

Perlite is a hydrated natural glass containing typically about 72-75% $SiO_2$, 12-14% $Al_2O_3$, 0.5-2% $Fe_2O_3$, 3-5% $Na_2O$, 4-5% $K_2O$, 0.4-1.5% CaO (by weight), and small concentrations of other metallic elements. Perlite is distinguished from other natural glasses by a higher content (2-10% by weight) of chemically bonded water, the presence of a vitreous, pearly luster, and characteristic concentric or arcuate onion skin-like (i.e., perlitic) fractures. Perlite flakes may be prepared by methods disclosed in WO02/11882 which may include milling, screening, and thermal expansion. Perlite flakes with controlled particle size distribution, low floater content, and high blue light brightness are preferred.

Perlite flakes having a median particle size of less than 50 microns are preferred. Perlite flakes having a median particle size of from 15-50 microns are preferred and perlite flakes having a median particle size of from 20-40 microns are most preferred.

The perlite flakes have a floater content of less than 10 percent by volume; especially a floater content of less than 5 percent by volume; very especially a floater content of less than 2 percent by volume. The perlite flakes have a blue light brightness greater than 80; especially greater than 82; very especially greater than 85.

The perlite flakes used in the present invention are not of a uniform shape. Nevertheless, for purposes of brevity, the perlite flakes will be referred to as having a "diameter." The perlite flakes have an average thickness of <2 µm, especially of from 200 to 1000 nm, especially from 200 to 600 nm. It is presently preferred that the diameter (median particle size ($d_{50}$)) of the flakes be in a preferred range of about 15-50 µm with a more preferred range of about 20-40 µm. If a $TiO_2$ layer is deposited as a material of high refractive index, the $TiO_2$ layer has a thickness of 20 to 300 nm, especially 20 to 100 nm, and more especially 20 to 50 nm.

The $Fe_2O_3$ content of the perlite is preferably below 2%, especially 0%.

The at present most preferred perlite is Optimat™ 2550 (World Minerals). Perlites, like Optimat™ 1735 (World Minerals) could also be used, if particles having a particle size below 10 µm are removed, for example, by sedimentation, or centrifugation.

If the perlite substrates of the present invention are used, interference pigments having superior brilliance, clear and intense colors, intense color flop, improved color strength and/or color purity can be obtained.

Metallic or non-metallic, inorganic platelet-shaped particles or pigments are effect pigments, (especially metal effect pigments or interference pigments), that is to say, pigments that, besides imparting colour to an application medium, impart additional properties, for example angle dependency of the colour (flop), lustre (not surface gloss) or texture. On metal effect pigments, substantially oriented reflection occurs at directionally oriented pigment particles. In the case of interference pigments, the colour-imparting effect is due to the phenomenon of interference of light in thin, highly refractive layers.

The (effect) pigments according to the invention can be used for all customary purposes, for example for colouring polymers in the mass, coatings (including effect finishes, including those for the automotive sector) and printing inks (including offset printing, intaglio printing, bronzing and flexographic printing), and also, for example, for applications in cosmetics, in ink-jet printing, for dyeing textiles, glazes for ceramics and glass as well as laser marking of papers and plastics. Such applications are known from reference works, for example "Industrielle Organische Pigmente" (W. Herbst and K. Hunger, VCH Verlagsgesellschaft mbH, Weinheim/New York, 2nd, completely revised edition, 1995).

When the pigments according to the invention are interference pigments (effect pigments), they may be goniochromatic and result in brilliant, highly saturated (lustrous) colours. They are accordingly very especially suitable for combination with conventional, transparent pigments, for example organic pigments such as, for example, diketopyrrolopyrroles, quinacridones, dioxazines, perylenes, isoindolinones etc., it being possible for the transparent pigment to have a similar colour to the effect pigment. Especially interesting combination effects are obtained, however, in analogy to, for example, EP-A-388 932 or EP-A-402 943, when the colour of the transparent pigment and that of the effect pigment are complementary.

The pigments according to the invention can be used with excellent results for pigmenting high molecular weight organic material.

The high molecular weight organic material for the pigmenting of which the pigments or pigment compositions according to the invention may be used may be of natural or synthetic origin. High molecular weight organic materials usually have molecular weights of about from $10^3$ to $10^8$ g/mol or even more. They may be, for example, natural resins, drying oils, rubber or casein, or natural substances derived therefrom, such as chlorinated rubber, oil-modified alkyd resins, viscose, cellulose ethers or esters, such as ethylcellulose, cellulose acetate, cellulose propionate, cellulose acetobutyrate or nitrocellulose, but especially totally synthetic organic polymers (thermosetting plastics and thermoplastics), as are obtained by polymerisation, polycondensation or polyaddition. From the class of the polymerisation resins there may be mentioned, especially, polyolefins, such as polyethylene, polypropylene or polyisobutylene, and also substituted polyolefins, such as polymerisation products of vinyl chloride, vinyl acetate, styrene, acrylonitrile, acrylic acid esters, methacrylic acid esters or butadiene, and also copolymerisation products of the said monomers, such as especially ABS or EVA.

From the series of the polyaddition resins and polycondensation resins there may be mentioned, for example, condensation products of formaldehyde with phenols, so-called phenoplasts, and condensation products of formaldehyde with urea, thiourea or melamine, so-called aminoplasts, and the polyesters used as surface-coating resins, either saturated, such as alkyd resins, or unsaturated, such as maleate resins; also linear polyesters and polyamides, polyurethanes or silicones.

The said high molecular weight compounds may be present singly or in mixtures, in the form of plastic masses or melts. They may also be present in the form of their monomers or in the polymerised state in dissolved form as film-formers or binders for coatings or printing inks, such as, for example, boiled linseed oil, nitrocellulose, alkyd resins, melamine resins and urea-formaldehyde resins or acrylic resins.

Depending on the intended purpose, it has proved advantageous to use the effect pigments or effect pigment compositions according to the invention as toners or in the form of preparations. Depending on the conditioning method or intended application, it may be advantageous to add certain amounts of texture-improving agents to the effect pigment before or after the conditioning process, provided that this has no adverse effect on use of the effect pigments for colouring high molecular weight organic materials, especially polyethylene. Suitable agents are, especially, fatty acids containing at least 18 carbon atoms, for example stearic or behenic acid, or amides or metal salts thereof, especially magnesium salts, and also plasticisers, waxes, resin acids, such as abietic acid, rosin soap, alkylphenols or aliphatic alcohols, such as stearyl alcohol, or aliphatic 1,2-dihydroxy compounds containing from 8 to 22 carbon atoms, such as 1,2-dodecanediol, and also modified colophonium maleate resins or fumaric acid colophonium resins. The texture-improving agents are added in amounts of preferably from 0.1 to 30% by weight, especially from 2 to 15% by weight, based on the end product.

The (effect) pigments according to the invention can be added in any tinctorially effective amount to the high molecular weight organic material being pigmented. A pigmented substance composition comprising a high molecular weight organic material and from 0.01 to 80% by weight, preferably from 0.1 to 30% by weight, based on the high molecular weight organic material, of an pigment according to the invention is advantageous. Concentrations of from 1 to 20% by weight, especially of about 10% by weight, can often be used in practice.

High concentrations, for example those above 30% by weight, are usually in the form of concentrates ("masterbatches") which can be used as colorants for producing pigmented materials having a relatively low pigment content, the pigments according to the invention having an extraordinarily low viscosity in customary formulations so that they can still be processed well.

For the purpose of pigmenting organic materials, the effect pigments according to the invention may be used singly. It is, however, also possible, in order to achieve different hues or colour effects, to add any desired amounts of other colour-imparting constituents, such as white, coloured, black or effect pigments, to the high molecular weight organic substances in addition to the effect pigments according to the invention. When coloured pigments are used in admixture with the effect pigments according to the invention, the total amount is preferably from 0.1 to 10% by weight, based on the high molecular weight organic material. Especially high goniochromicity is provided by the preferred combination of an effect pigment according to the invention with a coloured pigment of another colour, especially of a complementary colour, with colorations made using the effect pigment and colorations made using the coloured pigment having, at a measurement angle of 10°, a difference in hue ($\Delta H^*$) of from 20 to 340, especially from 150 to 210.

Preferably, the effect pigments according to the invention are combined with transparent coloured pigments, it being possible for the transparent coloured pigments to be present either in the same medium as the effect pigments according to the invention or in a neighbouring medium. An example of an arrangement in which the effect pigment and the coloured pigment are advantageously present in neighbouring media is a multi-layer effect coating.

The pigmenting of high molecular weight organic substances with the pigments according to the invention is carried out, for example, by admixing such a pigment, where appropriate in the form of a masterbatch, with the substrates using roll mills or mixing or grinding apparatuses. The pigmented material is then brought into the desired final form using methods known per se, such as calendering, compression moulding, extrusion, coating, pouring or injection moulding. Any additives customary in the plastics industry, such as plasticisers, fillers or stabilisers, can be added to the polymer, in customary amounts, before or after incorporation of the pigment. In particular, in order to produce non-rigid shaped articles or to reduce their brittleness, it is desirable to add plasticisers, for example esters of phosphoric acid, phthalic acid or sebacic acid, to the high molecular weight compounds prior to shaping.

For pigmenting coatings and printing inks, the high molecular weight organic materials and the effect pigments according to the invention, where appropriate together with customary additives such as, for example, fillers, other pigments, siccatives or plasticisers, are finely dispersed or dissolved in the same organic solvent or solvent mixture, it being possible for the individual components to be dissolved or dispersed separately or for a number of components to be dissolved or dispersed together, and only thereafter for all the components to be brought together.

Dispersing an effect pigment according to the invention in the high molecular weight organic material being pigmented, and processing a pigment composition according to the invention, are preferably carried out subject to conditions under which only relatively weak shear forces occur so that the effect pigment is not broken up into smaller portions.

Plastics comprising the pigment of the invention in amounts of 0.1 to 50% by weight, in particular 0.5 to 7% by weight. In the coating sector, the pigments of the invention are employed in amounts of 0.1 to 10% by weight. In the pigmentation of binder systems, for example for paints and printing inks for intaglio, offset or screen printing, the pigment is incorporated into the printing ink in amounts of 0.1 to 50% by weight, preferably 5 to 30% by weight and in particular 8 to 15% by weight.

The colorations obtained, for example in plastics, coatings or printing inks, especially in coatings or printing inks, more especially in coatings, may be distinguished by excellent properties, especially by extremely high saturation, outstanding fastness properties, high color purity and high goniochromaticity.

When the high molecular weight material being pigmented is a coating, it is especially a speciality coating, very especially an automotive finish.

The effect pigments according to the invention are also suitable for making-up the lips or the skin and for colouring the hair or the nails.

The invention accordingly relates also to a cosmetic preparation or formulation comprising from 0.0001 to 90% by weight of a pigment, especially an effect pigment, according to the invention and from 10 to 99.9999% of a cosmetically suitable carrier material, based on the total weight of the cosmetic preparation or formulation.

Such cosmetic preparations or formulations are, for example, lipsticks, blushers, foundations, nail varnishes and hair shampoos.

The pigments may be used singly or in the form of mixtures. It is, in addition, possible to use pigments according to the invention together with other pigments and/or colorants, for example in combinations as described hereinbefore or as known in cosmetic preparations.

The cosmetic preparations and formulations according to the invention preferably contain the pigment according to the invention in an amount from 0.005 to 50% by weight, based on the total weight of the preparation.

Suitable carrier materials for the cosmetic preparations and formulations according to the invention include the customary materials used in such compositions.

The cosmetic preparations and formulations according to the invention may be in the form of, for example, sticks, ointments, creams, emulsions, suspensions, dispersions, powders or solutions. They are, for example, lipsticks, mascara preparations, blushers, eye-shadows, foundations, eyeliners, powder or nail varnishes.

If the preparations are in the form of sticks, for example lipsticks, eye-shadows, blushers or foundations, the preparations consist for a considerable part of fatty components, which may consist of one or more waxes, for example ozokerite, lanolin, lanolin alcohol, hydrogenated lanolin, acetylated lanolin, lanolin wax, beeswax, candelilla wax, microcrystalline wax, carnauba wax, cetyl alcohol, stearyl alcohol, cocoa butter, lanolin fatty acids, petrolatum, petroleum jelly, mono-, di- or tri-glycerides or fatty esters thereof that are solid at 25° C., silicone waxes, such as methyloctadecane-oxypolysiloxane and poly(dimethylsiloxy)-stearoxysiloxane, stearic acid monoethanolamine, colophane and derivatives thereof, such as glycol abietates and glycerol abietates, hydrogenated oils that are solid at 25° C., sugar glycerides and oleates, myristates, lanolates, stearates and dihydroxystearates of calcium, magnesium, zirconium and aluminium.

The fatty component may also consist of a mixture of at least one wax and at least one oil, in which case the following oils, for example, are suitable: paraffin oil, purcelline oil, perhydrosqualene, sweet almond oil, avocado oil, calophyllum oil, castor oil, sesame oil, jojoba oil, mineral oils having a boiling point of about from 310 to 410° C., silicone oils, such as dimethylpolysiloxane, linoleyl alcohol, linolenyl alcohol, oleyl alcohol, cereal grain oils, such as wheatgerm oil, isopropyl lanolate, isopropyl palmitate, isopropyl myristate, butyl myristate, cetyl myristate, hexadecyl stearate, butyl stearate, decyl oleate, acetyl glycerides, octanoates and decanoates of alcohols and polyalcohols, for example of glycol and glycerol, ricinoleates of alcohols and polyalcohols, for example of cetyl alcohol, isostearyl alcohol, isocetyl lanolate, isopropyl adipate, hexyl laurate and octyl dodecanol.

The fatty components in such preparations in the form of sticks may generally constitute up to 99.91% by weight of the total weight of the preparation.

The cosmetic preparations and formulations according to the invention may additionally comprise further constituents, such as, for example, glycols, polyethylene glycols, polypropylene glycols, monoalkanolamides, non-coloured polymeric, inorganic or organic fillers, preservatives, UV filters or other adjuvants and additives customary in cosmetics, for example a natural or synthetic or partially synthetic di- or tri-glyceride, a mineral oil, a silicone oil, a wax, a fatty alcohol, a Guerbet alcohol or ester thereof, a lipophilic functional cosmetic active ingredient, including sun-protection filters, or a mixture of such substances.

A lipophilic functional cosmetic active ingredient suitable for skin cosmetics, an active ingredient composition or an active ingredient extract is an ingredient or a mixture of ingredients that is approved for dermal or topical application. The following may be mentioned by way of example:

active ingredients having a cleansing action on the skin surface and the hair; these include all substances that serve to cleanse the skin, such as oils, soaps, synthetic detergents and solid substances;

active ingredients having a deodorising and perspiration-inhibiting action: they include antiperspirants based on aluminium salts or zinc salts, deodorants comprising bactericidal or bacteriostatic deodorising substances, for example triclosan, hexachlorophene, alcohols and cationic substances, such as, for example, quaternary ammonium salts, and odour absorbers, for example ®Grillocin (combination of zinc ricinoleate and various additives) or triethyl citrate (optionally in combination with an antioxidant, such as, for example, butyl hydroxytoluene) or ion-exchange resins;

active ingredients that offer protection against sunlight (UV filters): suitable active ingredients are filter substances (sunscreens) that are able to absorb UV radiation from sunlight and convert it into heat; depending on the desired action, the following light-protection agents are preferred: light-protection agents that selectively absorb sunburn-causing high-energy UV radiation in the range of approximately from 280 to 315 nm (UV-B absorbers) and transmit the longer-wavelength range of, for example, from 315 to 400 nm (UV-A range), as well as light-protection agents that absorb only the longer-wavelength radiation of the UV-A range of from 315 to 400 nm (UV-A absorbers); suitable light-protection agents are, for example, organic UV absorbers from the class of the p-aminobenzoic acid derivatives, salicylic acid derivatives, benzophenone derivatives, dibenzoylmethane derivatives, diphenyl acrylate derivatives, benzofuran derivatives, polymeric UV absorbers comprising one or more organosilicon radicals, cinnamic acid derivatives, camphor derivatives, trianilino-s-triazine derivatives, phenyl-benzimidazolesulfonic acid and salts thereof, menthyl anthranilates, benzotriazole derivatives, and/or an inorganic micropigment selected from aluminium oxide- or silicon dioxide-coated $TiO_2$, zinc oxide or mica;

active ingredients against insects (repellents) are agents that are intended to prevent insects from touching the skin and becoming active there; they drive insects away and evaporate slowly; the most frequently used repellent is diethyl toluamide (DEET); other common repellents will be found, for example, in "Pflegekosmetik" (W. Raab and U. Kindl, Gustav-Fischer-Verlag Stuttgart/New York, 1991) on page 161;

active ingredients for protection against chemical and mechanical influences: these include all substances that form a barrier between the skin and external harmful substances, such as, for example, paraffin oils, silicone oils, vegetable oils, PCL products and lanolin for protection against aqueous solutions, film-forming agents, such as sodium alginate, triethanolamine alginate, polyacrylates, polyvinyl alcohol or cellulose ethers for protection against the effect of organic solvents, or substances based on mineral oils, vegetable oils or silicone oils as "lubricants" for protection against severe mechanical stresses on the skin;

moisturising substances: the following substances, for example, are used as moisture-controlling agents (moisturisers): sodium lactate, urea, alcohols, sorbitol, glycerol, propylene glycol, collagen, elastin and hyaluronic acid;

active ingredients having a keratoplastic effect: benzoyl peroxide, retinoic acid, colloidal sulfur and resorcinol;

antimicrobial agents, such as, for example, triclosan or quaternary ammonium compounds;

oily or oil-soluble vitamins or vitamin derivatives that can be applied dermally: for example vitamin A (retinol in the form of the free acid or derivatives thereof), panthenol, pantothenic acid, folic acid, and combinations thereof, vitamin E (tocopherol), vitamin F; essential fatty acids; or niacinamide (nicotinic acid amide);

vitamin-based placenta extracts: active ingredient compositions comprising especially vitamins A, C, E, $B_1$, $B_2$, $B_6$, $B_{12}$, folic acid and biotin, amino acids and enzymes as well as compounds of the trace elements magnesium, silicon, phosphorus, calcium, manganese, iron or copper;

skin repair complexes: obtainable from inactivated and disintegrated cultures of bacteria of the bifidus group;

plants and plant extracts: for example arnica, aloe, beard lichen, ivy, stinging nettle, ginseng, henna, camomile, marigold, rosemary, sage, horsetail or thyme;

animal extracts: for example royal jelly, propolis, proteins or thymus extracts;

cosmetic oils that can be applied dermally: neutral oils of the Miglyol 812 type, apricot kernel oil, avocado oil, babassu oil, cottonseed oil, borage oil, thistle oil, groundnut oil, gamma-oryzanol, rosehip-seed oil, hemp oil, hazelnut oil, blackcurrant-seed oil, jojoba oil, cherry-stone oil, salmon oil, linseed oil, cornseed oil, macadamia nut oil, almond oil, evening primrose oil, mink oil, olive oil, pecan nut oil, peach kernel oil, pistachio nut oil, rape oil, rice-seed oil, castor oil, safflower oil, sesame oil, soybean oil, sunflower oil, tea tree oil, grapeseed oil or wheatgerm oil.

The preparations in stick form are preferably anhydrous but may in certain cases comprise a certain amount of water which, however, in general does not exceed 40% by weight, based on the total weight of the cosmetic preparation.

If the cosmetic preparations and formulations according to the invention are in the form of semi-solid products, that is to say in the form of ointments or creams, they may likewise be anhydrous or aqueous. Such preparations and formulations are, for example, mascaras, eyeliners, foundations, blushers, eye-shadows, or compositions for treating rings under the eyes.

If, on the other hand, such ointments or creams are aqueous, they are especially emulsions of the water-in-oil type or of the oil-in-water type that comprise, apart from the pigment, from 1 to 98.8% by weight of the fatty phase, from 1 to 98.8% by weight of the aqueous phase and from 0.2 to 30% by weight of an emulsifier.

Such ointments and creams may also comprise further conventional additives, such as, for example, perfumes, antioxidants, preservatives, gel-forming agents, UV filters, colorants, pigments, pearlescent agents, non-coloured polymers as well as inorganic or organic fillers.

If the preparations are in the form of a powder, they consist substantially of a mineral or inorganic or organic filler such as, for example, talcum, kaolin, starch, polyethylene powder or polyamide powder, as well as adjuvants such as binders, colorants etc.

Such preparations may likewise comprise various adjuvants conventionally employed in cosmetics, such as fragrances, antioxidants, preservatives etc.

If the cosmetic preparations and formulations according to the invention are nail varnishes, they consist essentially of nitrocellulose and a natural or synthetic polymer in the form of a solution in a solvent system, it being possible for the solution to comprise other adjuvants, for example pearlescent agents.

In that embodiment, the coloured polymer is present in an amount of approximately from 0.1 to 5% by weight.

The cosmetic preparations and formulations according to the invention may also be used for colouring the hair, in which case they are used in the form of shampoos, creams or gels that are composed of the base substances conventionally employed in the cosmetics industry and a pigment according to the invention.

The cosmetic preparations and formulations according to the invention are prepared in conventional manner, for example by mixing or stirring the components together, optionally with heating so that the mixtures melt.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

17 g of OptiMat™ 1735 are suspended in deionised water. The particles are let to settle during 30 minutes. The particles still in suspension are removed. This operation is repeated 5 times.

Then the sediment material is dispersed in 300 ml of deionised water and heated at 90° C. The pH of the suspension is set at 1.5 and 20 ml of a solution comprising 9 g of $SnCl_4/5H_2O$, 5 g of 37% HCl, 1.00 g glycine and 100 g distilled water is added at a speed of 0.4 ml per minute while keeping the pH constant with continuous addition of 1 molar NaOH. Then the pH is set at 1.8 and 467 ml of a solution comprising 34.00 g of $TiOCl_2$, 32 g of 37% HCl, 5.22 g glycine and 445 g distilled water are added at a speed of 1 ml per minute while keeping the pH at 1.8 with 1 M NaOH. 13.3 g of a bright blue powder, which shows a flop toward violet, are obtained after filtration, drying and calcination in air at 750° C. It was confirmed by X-ray spectroscopy that the coating consists of rutile $TiO_2$.

The invention claimed is:

1. An interference pigment comprising at least three alternating layers of high and low refractive index, layered structure comprising:
    a substrate comprising perlite flakes having a median particle size ($d_{50}$) of 15-50 μm, a floater content of less than 10 percent by volume, and a blue light brightness greater than 80;
    a first coating on the substrate having a refractive index >1.65 and comprising;
    a second coating disposed on the first coating and having a refractive index ≤1.65; and
    a third coating disposed on the second coating and having a refractive index >1.65.

2. The pigment of claim 1, wherein the thickness of the first coating is 20 to 350 nm.

3. The pigment of claim 1, wherein the thickness of the second coating is 30 to 600 nm.

4. The pigment of claim 1, wherein the thickness of the third coating is 20 to 350 nm.

5. The pigment of claim 1, wherein the first coating comprises a metal oxide, metal sulfide, or metal oxide mixture.

6. The pigment of claim 1, wherein the first coating comprises $TiO_2$, $Fe_2O_3$, $TiFe_2O_5$, $Fe_3O_4$, BiOCl, CoO, $Co_3O_4$, $Cr_2O_3$, $VO_2$, $V_2O_3$, $Sn(Sb)O_2$, $SnO_2$, $ZrO_2$, iron titanates, iron oxide hydrates, titanium suboxides, bismuth vanadate, cobalt aluminate, or any mixture thereof.

7. The pigment of claim 1, wherein the first coating comprises a sulfide of tin, silver, lanthanum, or rare earth metal.

8. The pigment of claim 1, wherein the second coating comprises $SiO_2$, $MgF_2$, $Al_2O_3$, AlOOH, $B_2O_3$, or a mixture thereof.

9. The pigment of claim 1, wherein the third coating comprises a colorless or colored metal oxide.

10. The pigment of claim 1, wherein the third coating comprises $TiO_2$, $Fe_2O_3$, $TiFe_2O_5$, $Fe_3O_4$, BiOCl, CoO, $Co_3O_4$, $Cr_2O_3$, $VO_2$, $V_2O_3$, $Sn(Sb)O_2$, $SnO_2$, $ZrO_2$, iron titanates, iron oxide hydrates, titanium suboxides, bismuth vanadate, cobalt aluminate, or any mixture thereof.

11. The pigment of claim 1 further comprising interlayers of absorbing or nonabsorbing materials between the first coating, the second coating, and the third coating.

12. The pigment of claim 11, wherein the thickness of the interlayers is 1 to 30 nm.

13. A composition comprising the pigment of claim 1, wherein the composition is a paint, printing ink, plastic, cosmetic, ceramic, or glass.

14. A method of using the pigment of claim 1 comprising incorporating the pigment in a coating; a printing ink; a plastic; a cosmetic; or a glaze for a ceramic or a glass.

15. A method for preparing the pigment of claim 1 comprising applying the first coating, the second coating, and the third coating by wet chemical coating.

16. The interference pigment of claim 1 which is:
Perlite/$TiO_2$/$SiO_2$/$TiO_2$;
Perlite/$TiO_2$/$SiO_2$/$Fe_2O_3$;
Perlite/$TiO_2$/$SiO_2$/$TiO_2.Fe_2O_3$;
Perlite/$TiO_2$/$SiO_2$/$(Sn,Sb)O_2$;
Perlite/$(Sn, Sb)O_2$/$SiO_2$/$TiO_2$;
Perlite/$Fe_2O_3$/$SiO_2$/$(Sn, Sb)O_2$;
Perlite/$TiO_2.Fe_2O_3$/$SiO_2$/$TiO_2.Fe_2O_3$;
Perlite/$TiO_2$/$SiO_2$/$MoS_2$;
Perlite/$TiO_2$/$SiO_2$/$Cr_2O_3$;
Perlite/$Cr_2O_3$/$SiO_2$/$TiO_2$;
Perlite/$Fe_2O_3$/$SiO_2$/$TiO_2$;
Perlite/$TiO_2$/$Al_2O_3$/$TiO_2$;
Perlite/$Fe_2TiO_5$/$SiO_2$/$TiO_2$;
Perlite/$TiO_2$/$SiO_2$/$Fe_2TiO_5$/$TiO_2$;
Perlite/TiO suboxides/$SiO_2$/TiO suboxides;
Perlite/$TiO_2$/$SiO_2$/$TiO_2$/$SiO_2$/$TiO_2$+Prussian Blue;
Perlite/$TiO_2$/$SiO_2$/$TiO_2$/$SiO_2$/$TiO_2$; or
Perlite/$TiO_2$/$SiO_2$/$TiO_2$/$SiO_2$/$TiO_2$/$SiO_2$/$TiO_2$.

* * * * *